(12) United States Patent
Cohen

(10) Patent No.: US 8,153,171 B1
(45) Date of Patent: *Apr. 10, 2012

(54) SOLUTION FOR DISSOLVING PRE-MELANOMA LESIONS AND MELANOMA LESIONS INCLUDING PSORIASIS, HERPES SIMPLEX LESIONS AND ECZEMA LESIONS

(76) Inventor: Allen Jay Cohen, St. Pete Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 12/927,878

(22) Filed: Nov. 29, 2010

Related U.S. Application Data

(63) Continuation-in-part of application No. 12/587,170, filed on Oct. 3, 2009, now abandoned, which is a continuation-in-part of application No. 12/286,258, filed on Sep. 29, 2008, now Pat. No. 7,597,914.

(60) Provisional application No. 60/977,060, filed on Oct. 2, 2007.

(51) Int. Cl.
*A61K 36/886* (2006.01)

(52) U.S. Cl. .................. 424/744; 514/179; 514/458

(58) Field of Classification Search .................. None
See application file for complete search history.

(56) References Cited

U.S. PATENT DOCUMENTS

| | | | | |
|---|---|---|---|---|
| 4,880,637 | A * | 11/1989 | Jordan | 424/641 |
| 5,604,258 | A * | 2/1997 | Ferrante et al. | 514/560 |
| 6,387,382 | B1 * | 5/2002 | Saleh et al. | 424/401 |
| 7,597,914 | B1 * | 10/2009 | Cohen | 424/744 |
| 2003/0017122 | A1 * | 1/2003 | Vromen | 424/59 |
| 2003/0129208 | A1 * | 7/2003 | Alberts et al. | 424/400 |
| 2003/0207818 | A1 * | 11/2003 | Jia et al. | 514/27 |
| 2005/0049202 | A1 * | 3/2005 | Kastelic et al. | 514/19 |
| 2005/0064025 | A1 * | 3/2005 | Litchenberger et al. | 424/450 |

OTHER PUBLICATIONS http://plants.usda.gov/java/profile?symbol=LATRT—accessed Mar. 2009.*

* cited by examiner

*Primary Examiner* — Susan Hoffman

(57) ABSTRACT

Alcohol constitutes a majority of the solution. Water, melaleuca alternifolia, amebicidal, acetate, aloe barbadensis, larrea tridentat and benzoic acid constitute a minority of the solution. The minority of the solution optionally includes a corticosteroid and a nutritional supplement.

2 Claims, No Drawings

SOLUTION FOR DISSOLVING PRE-MELANOMA LESIONS AND MELANOMA LESIONS INCLUDING PSORIASIS, HERPES SIMPLEX LESIONS AND ECZEMA LESIONS

RELATED APPLICATION

The present application is a continuation-in-part of non-provisional application Ser. No. 12/587,170 filed Oct. 3, 2009, now abandoned, which is a continuation-in-part of U.S. patent application Ser. No. 12/286,258 filed Sep. 29, 2008 issued Oct. 6, 2009 as U.S. Pat. No. 7,597,914 which in turn is based upon U.S. Provisional Application No. 60/977,060, filed Oct. 2, 2007, the subject matter of which applications is incorporated herein by reference.

BACKGROUND OF THE INVENTION

Field of the Invention

The present invention relates to a solution for dissolving pre-melanoma lesions and melanoma lesions including psoriasis, herpes simplex lesions and eczema lesions and more particularly pertains to dissolving pre-cancerous tumors and lesions of the skin.

SUMMARY OF THE INVENTION

In view of the disadvantages inherent in the known types of medicinal solutions of known designs and configurations now present in the prior art, the present invention provides an improved solution for dissolving pre-melanoma lesions and melanoma lesions including psoriasis, herpes simplex lesions and eczema lesions. As such, the general purpose of the present invention, which will be described subsequently in greater detail, is to provide a new and improved solution for dissolving pre-melanoma lesion and a melanoma lesion which has all the advantages of the prior art and none of the disadvantages.

To attain this, the present invention essentially comprises a solution for dissolving pre-melanoma lesions and melanoma lesions. First provided is a solution. The solution is a topical medication. The solution is comprised of anti-bacterial, anti-fungal and anti-viral elements. In this manner pre-cancerous tumors and lesions of the skin are dissolved. The specific solution, in the preferred embodiment, contains 60 percent by volume ethyl alcohol, 11 percent by volume purified water, 10 percent by volume melaleuca alternifolia, 5 percent by volume hydrocortisone, 5 percent by volume iodoquinol, 2 percent by volume tocopheryl acetate, 2 percent by volume aloe barbadensis, 2 percent by volume larrea tridentat, a mixture of 2 percent by volume oat flour, isopropyl and palmitate, and 1 percent by volume benzoic acid. The enumerated percentages herein are all by volume.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved solution for dissolving pre-melanoma lesions and melanoma lesions including psoriasis, herpes simplex lesions and eczema lesions which has all of the advantages of the prior art solutions of known designs and configurations and none of the disadvantages.

It is another object of the present invention to provide a new and improved solution for dissolving pre-melanoma lesions and melanoma lesions including psoriasis, herpes simplex lesions and eczema lesions which may be easily and efficiently manufactured and marketed.

It is further object of the present invention to provide a new and improved solution for dissolving pre-melanoma lesions and melanoma lesions including psoriasis, herpes simplex lesions and eczema lesions which is of durable and reliable constructions.

An even further object of the present invention is to provide a new and improved solution for dissolving pre-melanoma lesions and melanoma lesions including psoriasis, herpes simplex lesions and eczema lesions which is susceptible of a low cost of manufacture with regard to both materials and labor, and which accordingly is then susceptible of low prices of sale to the consuming public, thereby making such solution for dissolving pre-melanoma lesions and melanoma lesions including psoriasis, herpes simplex lesions and eczema lesions economically available to the buying public.

Lastly, it is an object of the present invention to provide a new and improved solution for dissolving pre-melanoma lesions and melanoma lesions including psoriasis, herpes simplex lesions and eczema lesions. Alcohol constitutes a majority of the solution and water, melaleuca alternifolia, amebicidal, acetate, aloe barbadensis, larrea tridentat and benzoic acid constitute a minority of the solution. The minority of the solution optionally includes a corticosteroid and a nutritional supplement. As used herein majority means in excess of 50 percent by volume. As used herein minority means less than 50 percent by volume.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the descriptive matter in which there is illustrated preferred embodiments of the invention.

DESCRIPTION OF THE PREFERRED EMBODIMENT

The preferred embodiment of the new and improved solution for dissolving pre-melanoma lesions and melanoma lesions including psoriasis, herpes simplex lesions and eczema lesions embodying the principles and concepts of the present invention and generally designated by the reference numeral will be described.

The present invention, a solution for dissolving pre-melanoma lesions and melanoma lesions including psoriasis, herpes simplex lesions and eczema lesions is comprised of a plurality of components. Such components in their broadest context include alcohol as a majority of a solution and a plurality of components as a minority of a solution. Such components are individually configured and correlated with respect to each other so as to attain the desired objective.

First provided is a solution. The solution is a topical medication. The solution is comprised of anti-bacterial, anti-fungal and anti-viral elements. In this manner pre-cancerous tumors and lesions of the skin are dissolved. The specific solution of the preferred embodiment contains 60 percent by volume ethyl alcohol, 11 percent by volume purified water, 10 percent by volume melaleuca alternifolia, 5 percent by volume hydrocortisone, 5 percent by volume iodoquinol, 2 percent by volume tocopheryl acetate, 2 percent by volume aloe barbadensis, 2 percent by volume larrea tridentat, a mixture of 2 percent by volume oat flour, isopropyl and palmitate, and 1 percent by volume benzoic acid. As used herein, all enumerated percentages are by volume. The larrea tridentata provides anti-viral affects for herpes lesions and is useful in dissolvong lesions as in eczema and psoriasis. The benzoic acid is used as a fungacide. It is also used in skin products, as a facial cleanser and anti-aging moisturizer. In addition, it is also useful in dissolving lesions as in eczema and herpes simplex lesions.

The invention from a broader standpoint is a solution comprising alcohol constituting a majority of the solution and water, melaleuca alternifolia, amebicidal, acetate, aloe barbadensis, larrea tridentat and benzoic acid constituting a minority of the solution minority of the solution.

Optionally, the minority of the solution further includes a corticosteroid. As a further option, the minority of the solution further includes a corticosteroid and a nutritional supplement.

The alcohol is chosen from the class of alcohols which includes ethyl alcohol and denatured ethanol.

The water is chosen from the class of waters, which includes purified water and distilled water.

The amebicidal is chosen from the class of amebicidals which includes iodoquinol and quinoline phosphate.

The acetate is chosen from the class of acetates which includes tocopheryl acetate and alpha-tocopheryl acetate.

The corticosteroid is chosen from the class of corticosteroids which includes hydrocortisone and pramoxine hydrochloride.

The nutritional supplement is chosen from the class of nutritional supplements which includes oat flour, isopropyl palmitate, cornflower, hybrid safflower oil, kaolin, rye flour and glycerin.

The alcohol constitutes between 57 and 66 percent by volume of the solution. The water constitutes between 7 and 16 percent by volume of the solution. Melaleuca alternifolia constitutes between 8 and 12 percent by volume of the solution. The cortcosteroid and the amebucidal each constitute between 3 and 7 percent by volume of the solution. The acetate, aloe barbadensis, larrea tridentat, nutritional supplement and benzoic acid each constitute between 1 and 3 percent by volume of the solution.

Various alternate embodiments and examples of the solution are as follows:

EXAMPLE I

Minimum Components for Ala-Septic Formulation

Broadest quantitive ranges
Ethyl Alcohol (62-70%)
Purified Water (13-21%)
Melaleuca Alternifolia (8-12%)
Iodoquinol (3-7%)
Tocopheryl Acetate (1-3%)

EXAMPLE II

Minimum Components for Ala-Septic Formulation

Mid-range quantitive ranges
Ethyl Alcohol (64-68%)
Purified Water (15-19%)
Melaleuca Alternifolia (9-11%)
Iodoquinol (4-6%)
Tocopheryl Acetate (1-3%)

EXAMPLE III

Minimum Components for Ala-Septic Formulation

Exact Preferred Quantitive Ranges
Ethyl Alcohol (66%)
Purified Water (17%)
Melaleuca Alternifolia (10%)
Iodoquinol (5%)
Tocopheryl Acetate (2%)

EXAMPLE IV

Minimum Components for Ala-Septic Formulation

Plus One Component
Broadest Quantitive Ranges
Ethyl Alcohol (62-70%)
Purified Water (13-19%)
Melaleuca Alternifolia (8-12%)
Iodoquinol (3-7%)
Tocopheryl Acetate (1-3%)
Benzoic Acid (1-3%)

EXAMPLE V

Minimum Components for Ala-Septic Formulation

Plus One Component
Mid-range Quantitive Ranges
Ethyl Alcohol (64-68%)
Purified Water (14-18%)
Melaleuca Alternifolia (9-11%)
Iodoquinol (4-6%)
Tocopheryl Acetate (1-3%)
Benzoic Acid (1-2%)

EXAMPLE VI

Minimum Components for Ala-Septic Formulation

Plus One Component
Exact Preferred Quantitive Ranges
Ethyl Alcohol (66%)
Purified Water (16%)
Melaleuca Alternifolia (10%)
Iodoquinol (5%)
Tocopheryl Acetate (2%)
Benzoic Acid (1%)

EXAMPLE VII

Minimum Components for Ala-Septic Formulation

Plus Two Components
Broadest Quantitive Ranges
Ethyl Alcohol (62-68%)
Purified Water (11-19%)
Melaleuca Alternifolia (8-12%)
Iodoquinol (3-7%)
Tocopheryl Acetate (1-3%)
Benzoic Acid (1-3%)
Larrea Tridentata (1-3%)

EXAMPLE VIII

Minimum Components for Ala-Septic Formulation

Plus Two Components
Mid-range Quantitive Ranges
Ethyl Alcohol (63-67%)
Purified Water (13-17%)
Melaleuca Alternifolia (9-11%)
Iodoquinol (4-6%)
Tocopheryl Acetate (1-3%)
Benzoic Acid (1-2%)
Larrea Tridentata (1-3%)

EXAMPLE IX

Minimum Components for Ala-Septic Formulation

Plus Two Components
Exact Preferred Quantitive Ranges
Ethyl Alcohol (65%)
Purified Water (15%)
Melaleuca Alternifolia (10%)
Iodoquinol (5%)
Tocopheryl Acetate (2%)
Benzoic Acid (1%)
Larrea Tridentata (2%)

EXAMPLE X

Minimum Components for Ala-Septic Formulation

Plus Three Components
Broadest Quantitive Ranges
Ethyl Alcohol (61-67%)
Purified Water (11-17%)
Melaleuca Alternifolia (8-12%)
Iodoquinol (3-7%)
Tocopheryl Acetate (1-3%)
Benzoic Acid (1-3%)
Larrea Tridentata (1-3%)
Aloe Barbadensis (1-3%)

EXAMPLE XI

Minimum Components for Ala-Septic Formulation

Plus Three Components
Mid-range Quantitive Ranges
Ethyl Alcohol (62-66%)
Purified Water (12-16%)
Melaleuca Alternifolia (9-11%)
Iodoquinol (4-6%)
Tocopheryl Acetate (1-3%)
Benzoic Acid (1-2%)
Larrea Tridentata (1-3%)
Aloe Barbadensis (1-3%)

EXAMPLE XII

Minimum Components for Ala-Septic Formulation

Plus Three Components
Exact Preferred Quantitive Ranges
Ethyl Alcohol (64%)
Purified Water (14%)
Melaleuca Alternifolia (10%)
Iodoquinol (5%)
Tocopheryl Acetate (2%)
Benzoic Acid (1%)
Larrea Tridentate (2%)
Aloe Barbadensis (2%)

EXAMPLE XIII

Minimum Components for Ala-Septic Formulation

Plus Four Components
Broadest Quantitive Ranges
Ethyl Alcohol (58-64%)
Purified Water (8-16%)
Melaleuca Alternifolia (8-12%)
Iodoquinol (3-7%)
Tocopheryl Acetate (1-3%)
Benzoic Acid (1-3%)
Larrea Tridentate (1-3%)
Aloe Barbadensis (1-3%)
Hydrocortisone (3-7%)

EXAMPLE XIV

Minimum Components for Ala-Septic Formulation

Plus Four Components
Mid-range Quantitive Ranges
Ethyl Alcohol (59-63%)
Purified Water (9-15%)
Melaleuca Alternifolia (9-11%)
Iodoquinol (4-6%)
Tocopheryl Acetate (1-3%)
Benzoic Acid (1-2%)
Larrea Tridentata (1-3%)
Aloe Barbadensis (1-3%)
Hydrocortisone (4-6%)

EXAMPLE XV

Minimum Components for Ala-Septic Formulation

Plus Four Components
Exact Preferred Quantitive Ranges
Ethyl Alcohol (61%)
Purified Water (12%)
Melaleuca Alternifolia (10%)
Iodoquinol (5%)
Tocopheryl Acetate (2%)
Benzoic Acid (1%)
Larrea Tridentate (2%)
Aloe Barbadensis (2%)
Hydrocortisone (5%)

EXAMPLE XVI

Minimum Components for Ala-Septic Formulation

Plus Five Components
Broadest Quantitive Ranges
Ethyl Alcohol (57-63%)
Purified Water (7-15%)
Melaleuca Alternifolia (8-12%)
Iodoquinol (3-7%)
Tocopheryl Acetate (1-3%)
Benzoic Acid (1-3%)
Larrea Tridentata (1-3%)
Aloe Barbadensis (1-3%)
Hydrocortisone (3-7%)
Oat flour, Isopropyl Palmitate (1-3%)

EXAMPLE XVII

Minimum Components for Ala-Septic Formulation

Plus Five Components
Mid-range Quantitive Ranges
Ethyl Alcohol (58-62%)
Purified Water (8-14%)
Melaleuca Alternifolia (9-11%)
Iodoquinol (4-6%)
Tocopheryl Acetate (1-3%)
Benzoic Acid (1-2%)
Larrea Tridentata (1-3%)
Aloe Barbadensis (1-3%)
Hydrocortisone (4-6%)
Oat flour, Isopropyl Palmitate (1-3%)

EXAMPLE XVIII

Minimum Components for Ala-Septic Formulation

Plus Five Components
Exact Preferred Quantitive Ranges
Ethyl Alcohol (60%)
Purified Water (11%)
Melaleuca Alternifolia (10%)
Iodoquinol (5%)
Tocopheryl Acetate (2%)
Benzoic Acid (1%)
Larrea Tridentata (2%)
Aloe Barbadensis (2%)
Hydrocortisone (5%)
Oat flour, Isopropyl Palmitate (2%)

The present invention also includes the method of dissolving pre-cancerous tumors and lesions of the skin. Such method includes the steps of first providing a solution for dissolving pre-melanoma lesions and melanoma lesions comprising alcohol constituting a majority of the solution and water, melaleuca alternifolia, amebicidal, acetate, aloe barbadensis, larrea tridentat and acid constituting a minority of the solution. The second step is applying the provided solution to each pre-cancerous and malignant lesion at least three times in a 24 hour period.

The components of the solution function together by eliminating bacteria, virus and fungus thereby dissolving the pre-cancerous tumors and lesions. As a result the natural immune system of the body is permitted to completely heal the tumor or lesion.

The solution can also be used to speed the healing processes of the skin when cuts, bruises, and abrasions are present. It helps irritating rashes to heal quickly and painlessly.

The solution of the present invention was primarily developed for the treatment of melanoma. The invention is a topical medication adapted to completely and painlessly dissolve pre-cancerous tumors and lesions on the skin without any scaring thus leaving the derma in its natural color and texture. Application frequency should be at least 3 to 4 times in a 24 hour period, to each pre-cancerous or malignant lesion. Results become obvious in a matter of days.

The solution is part homeopathic and elements within it certainly require a pharmaceutical compounding. This is a unique formula in that it is anti-viral, anti-bacterial and anti-fungal. It functions without pain, burnings, surgery and most important without scaring. This type of medication is unique as it does not require any type of surgery. In additional to all of the above, it also appears to prevent or at the very least delay the formulation of Herbes lesions, a virus affecting some 50 million Americans, at the present time. The solution of the present invention achieves its objective by prevention of replicating the underlying viruses and actually dissolving the tumors and lesions on the surface of the skin, thereby permitting the natural healing process to function The solutions of the present invention have been tested on humans with pre-melanoma lesions and melanoma lesions including psoriasis, herpes simplex lesions and eczema lesions with surprisingly successful results.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A solution for dissolving pre-melanoma lesions, melanoma lesions, psoriasis lesions, herpes simplex lesions and eczema lesions consisting of:
    alcohol constituting a majority of the solution; and
    water, melaleuca alternifolia, amebicidal, acetate, aloe barbadensis, larrea tridentat and benzoic acid constituting less than 50 percent by volume of the solution, a minority of the solution, the amebicidal being chosen from the class of amebicidals consisting of iodoquinol and quinoline phosphate.

2. A topical solution for dissolving psoriasis lesions, herpes simplex lesions and eczema lesions, the solution comprising in combination:
    60 percent by volume ethyl alcohol;
    11 percent by volume purified water;
    10 percent by volume melaleuca alternifolia;
    5 percent by volume hydrocortisone;

5 percent by volume iodoquinol;
2 percent by volume tocopheryl acetate;
2 percent by volume aloe barbadensis;
2 percent by volume larrea tridentat;
a mixture of 2 percent by volume oat flour and isopropyl palmitate; and
1 percent by volume benzoic acid.

* * * * *